US00PP29844P3

(12) United States Plant Patent
Arnold et al.

(10) Patent No.: US PP29,844 P3
(45) Date of Patent: Nov. 13, 2018

(54) TX-10-G-L-11-9-12-5

(50) Latin Name: *Oenothera drummondii*
Varietal Denomination: TX-10-G-L-11-9-12-5

(71) Applicant: The Texas A&M University System, College Station, TX (US)

(72) Inventors: Michael A. Arnold, College Station, TX (US); Sean Carver, Johnston, IA (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/530,786

(22) Filed: Feb. 27, 2017

(65) Prior Publication Data

US 2018/0249618 P1 Aug. 30, 2018

(51) Int. Cl.
*A01H 5/00* (2018.01)

(52) U.S. Cl.
USPC ..... Plt./460

(58) Field of Classification Search
USPC ..... Plt./460
See application file for complete search history.

(56) References Cited

PUBLICATIONS

Carver, S.T., Evaluating the Ornamental Potentials of Four Native Texas Coastal Species, Ph.D. Dissertation, 2015, p. 155, Texas A&M University, College Station, Texas.

Carver, S.T. et al., Variation in vegetative and floral characteristics of potential commercial significance in four native Texas coastal species, Phytologia, Oct. 6, 2016, pp. 250-276, 98(4).

King, Andrew Richard, Investigating Asexual Propagation, Container Production, Drought Tolerance, and Marketing Strategies of Five Native Texas Groundcovers, Ph.D. Dissertation, Mar. 2015, Texas A&M University, College Station, Texas.

*Primary Examiner* — Annette H Para

(74) *Attorney, Agent, or Firm* — Ramey & Schwaller, LLP

(57) ABSTRACT

A new and distinct cultivar of *Oenothera drummondii* identified as TX-12-5 characterized by 1) a propensity for free flowering (numerous flowers over an extended time and range of photoperiods), 2) a low spreading growth habit (typically less than 30 cm tall) with a dense canopy of foliage, 3) a grey-green shade of foliage compared to the green of most of the species, and 4) consistently bright yellow flowers.

11 Drawing Sheets

Botanical classification: *Oenothera drummondii.*
Varietal denomination: TX-10-G-L-11-9-12-5.

CROSS-REFERENCE TO COPENDING APPLICATIONS n/a

BACKGROUND OF THE INVENTION

Field of the Invention

This invention relates to a new and distinct cultivar of *Oenothera drummondii* plant, botanically known as *Oenothera drummondii* TX-10-G-L-11-9-12-5 (herein referred to by the experimental designation TX-12-5). The market class of *Oenothera drummondii* is an evergreen to semi-evergreen perennial subshrub. The plant will be used as a bedding plant, groundcover, herbaceous perennial color, or low shrub where cold hardy or it is rapid enough growing to serve as a summer annual in regions where cold winters do not permit its survival year-round.

SUMMARY OF THE INVENTION

The TX-12-5 cultivar of *Oenothera drummondii* is characterized as to novelty and is otherwise noteworthy by low spreading dense growth habit, grey-green foliage color, free flowering propensity, bright yellow color of the large flowers, and ease of rooting of vegetative stem cuttings. Currently, no cultivars of this species are available in the U.S.A. nursery trade.

ORIGIN OF THE VARIETY

The present *Oenothera* was the result of recurrent mass selection efforts after initial collection of promising phenotypes from wild populations.

*Oenothera drummondii* TX-12-5 is a result of a clonal selection from among the third-generation populations of seedlings derived from recurrent mass selection procedures. Initial collections of promising phenotypes based on aesthetic qualities such as foliage color, flowering propensity, and growth habit were collected from across the Texas coastal range of *Oenothera drummondii* (Carver, 2015). These phenotypes were then screened in replicated trials in both field and container nursery environments for growth rates, flowering, and aesthetic qualities (Carver et al., 2016). From these screening efforts, open pollinated (male parent) seed was collected from a particularly promising test clone TX-10 (not patented) (female parent) originating from wild collections in 2010 from near Jamaica Beach on the Texas Gulf Coast. This seed was grown out and screened for the most promising phenotypes. From this population, a test seedling TX-10-G-L-11-9 (not patented) was selected. Seedling TX-10-G-L-11-9-12-5 was selected from seedlings of TX-10-G-L-11-9 and vegetatively propagated to test its stability across several environments. Trials with this genotype were conducted at several locations in Texas and then through material transfer agreements with EuroAmerican Propagators, tested in California, Chicago, and Florida to determine performances outside Texas. The original TX-10 phenotype from the wild collection exhibited a propensity for free flowering, but had a tall, looser, open habit and leaves that were green rather than the blue-green or grey-green compared to some of the other collected genotypes. This cultivar shows considerably less problems with root rots compared to the second-generation prior maternal parent plant. TX 12-5 is lower growing, denser of canopy, the foliage more blue-green, and sepals have a red stripe orange-red margin (R.H.S. N34A) than TX-10. Thus, the lower growing habit and more grey or bluish tint to the foliage are likely due to pollen contribution from other collected phenotypes during the recurrent mass selection process.

ASEXUAL REPRODUCTION OF THE VARIETY

Trials with *Oenothera drummondii* TX-12-5 were conducted at several Texas A&M AgriLife Research locations in Texas and then through material transfer agreements with EuroAmerican Propagators, where it was tested in California, Chicago, and Florida to determine performances outside Texas. The plant has been evaluated during the period from 2012-2016. This evaluation clearly demonstrated that the plants were true to the distinguishing characteristics of the parents in all observable aspects. Size and growth habits are estimated from two- to three-year-old plants growing in-ground where they have reached mature sizes.

BRIEF DESCRIPTION OF THE DRAWINGS

This new variety of *Oenothera drummondii* is illustrated by the accompanying photographic drawings and depicts the plant by the best possible color representation using color photography, wherein.

BOTANICAL DESCRIPTION OF THE VARIETY

Figure 1:
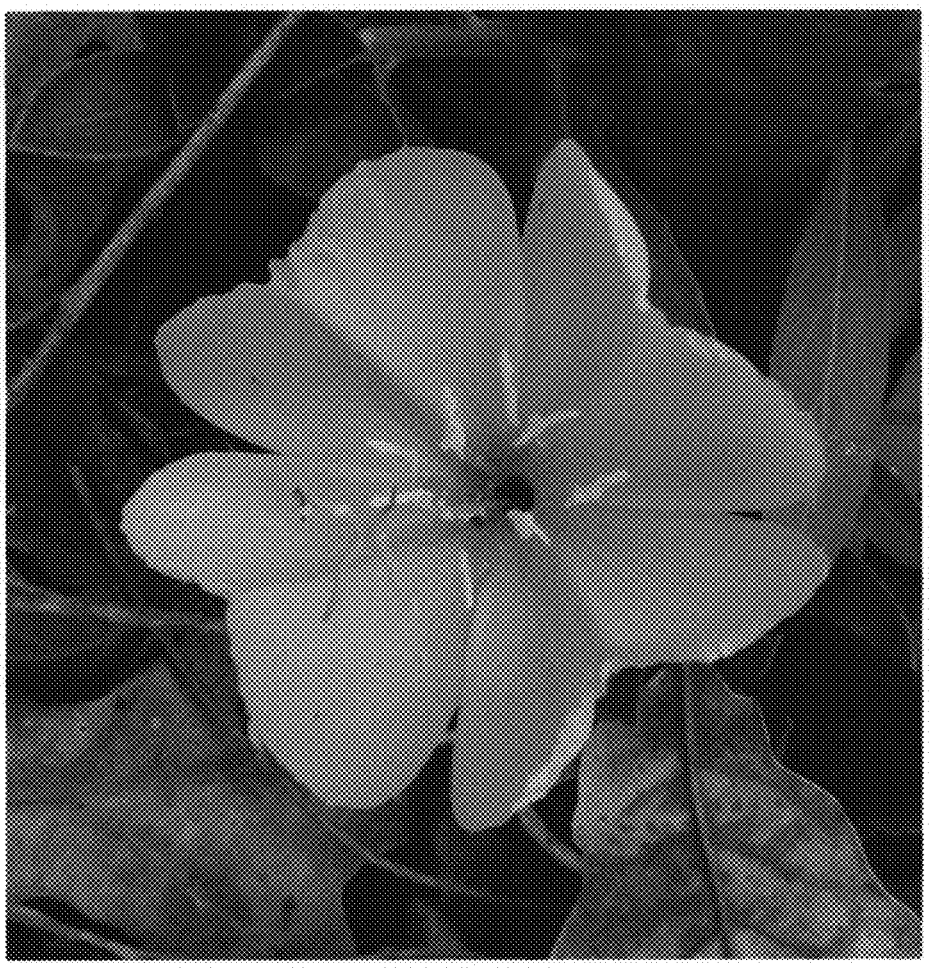
FIG. 1. Color photograph of top view of flower.

The following is a detailed description of the new variety. The following traits have been repeatedly observed and are determined to be the unique characteristics: 1) a propensity for free flowering (numerous flowers over an extended time and range of photoperiods) with strongly overlapping petals forming a cup-shaped flower and orange-red margins on the sepals, 2) a low spreading growth habit (typically less than 30 cm tall) with a dense canopy of foliage, 3) a grey-green shade of foliage compared to the green of most of the species, 4) consistently bright yellow flowers, 5) good field tolerance in *Phytophthora* infested soils, and 6) leaves broader in relation to their length than is typical of the species.

All major color code designations are by reference to The R.H.S. Colour Chart (Fourth Edition) provided by The Royal Horticultural Society of Great Britain. Colors are approximate as color depends on horticultural practices such as light level and fertilization rate, among others.

PLANT

Type: Evergreen to semi-evergreen perennial subshrub; life expectancy varies by location but typically is 3 to 5 years in cultivated landscapes where winters are not severe (USDA hardiness zones 8b to 13); can be grown as a summer annual in colder climates.

Classification: A vegetatively propagated cultivar derived from the species *Oenothera drummondii* Hook (not patented); this species is commonly known as beach evening primrose or coast evening primrose.

Origin: Original genotypes for the breeding efforts were obtained from collections from wild plants native throughout the Texas Gulf Coast from 26.06.879 N latitude to 29.40.203 N latitude then subjected to sequences of recurrent mass selection and finally clonal selection.

Parentage: The original female parent TX-10 originated from wild collections in 2010 from near Jamaica Beach (29.06.698 N latitude, 95.04.956 W longitude) on the Texas Gulf Coast. Male parents were uncertain as subsequent generations were obtained from open pollinated seeds; however due to the isolated plantings where the recurrent mass selection occurred, the male parents would be derived in some combination from genetic materials originating from along the Texas Gulf coast as these where the only *Oenothera drummondii* genotypes with pollination range. Given the infusion of genes for the grey shading in the foliage as indicated in attached figures, most likely at least one male parent would have been from the southern portion of the Texas Gulf Coast which is where the denser pubescence resulting in the grey-green foliage is more predominant (Carver, 2015; Carver et al., 2016). Although the original female parent TX-10 no longer exists, images of two other advanced clonal selections in our program, O-10 and O-6, are included for comparison of leaf shapes and stem characteristics. Images of O-10 flowers are included for comparison to those of TX-10-G-L-11-9-12-5 to illustrate the petal overlap and unique orange-red sepal characteristics of TX-10-G-L-11-9-12-5. *Oenothera drummondii* is currently a seldom encountered species commercially in the trade and no known cultivars have previously been introduced from this species of which we can ascertain.

Propagation: *Oenothera drummondii* roots in very high percentages under intermittent mist within 10 to 14 of sticking cuttings in 100% perlite substrate (King, 2015). Cuttings should be removed very soon after adventitious rooting occurs on the stems or fungal rots may occur if left under the mist too long. Substrate and fertility experiments indicate that various combinations of pine bark, peat moss, and perlite can be used to successfully grow plants in container culture (King, 2015). The combinations with approximately equal volumes of peat, perlite, and bark were suitable and this corresponds to the typical composition of many commercial nursery crop substrates.

Form: The density of foliage and horizontal crisscrossing of branching creates a solid canopy as a low groundcover.

Figure 5:
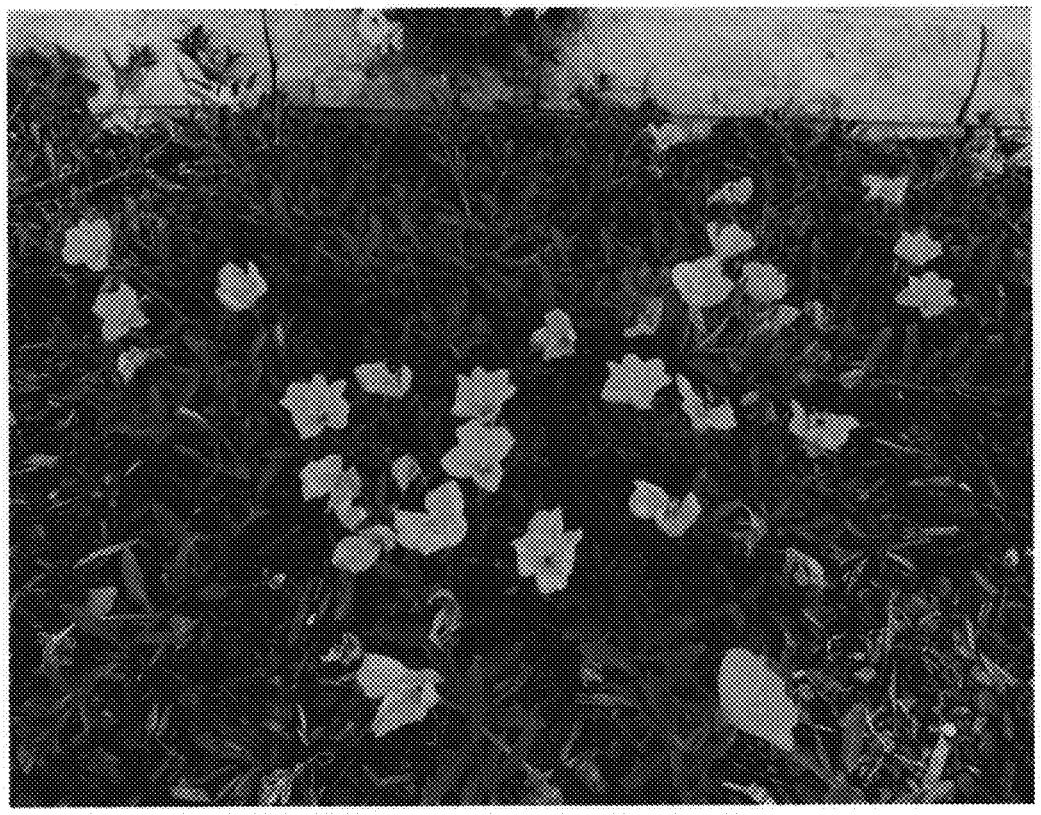
FIG. 5. Color photograph of three-month old plants in summer.

Mature habit: Low spreading dense canopy typically under 30 cm tall with branches originating from a woody base in contrast with the species in general which can reach up to 1 m in height (Richardson, 1990). FIG. 5 depicts TX-10-G-L-11-9-12-5, illustrating distinctive low growth habit.

Growth: Vigor is strong with growth occurring rapidly under favorable conditions; plants require well drained soils and sunny locations but will survive in partial shaded locations; greenhouse substrates should be well aerated with good drainage, but plants are soil pH-adaptable and originate from coastal locations, with salinity tolerance to irrigation with water containing half the salinity of seawater (Carver, 2015).

Figure 6:
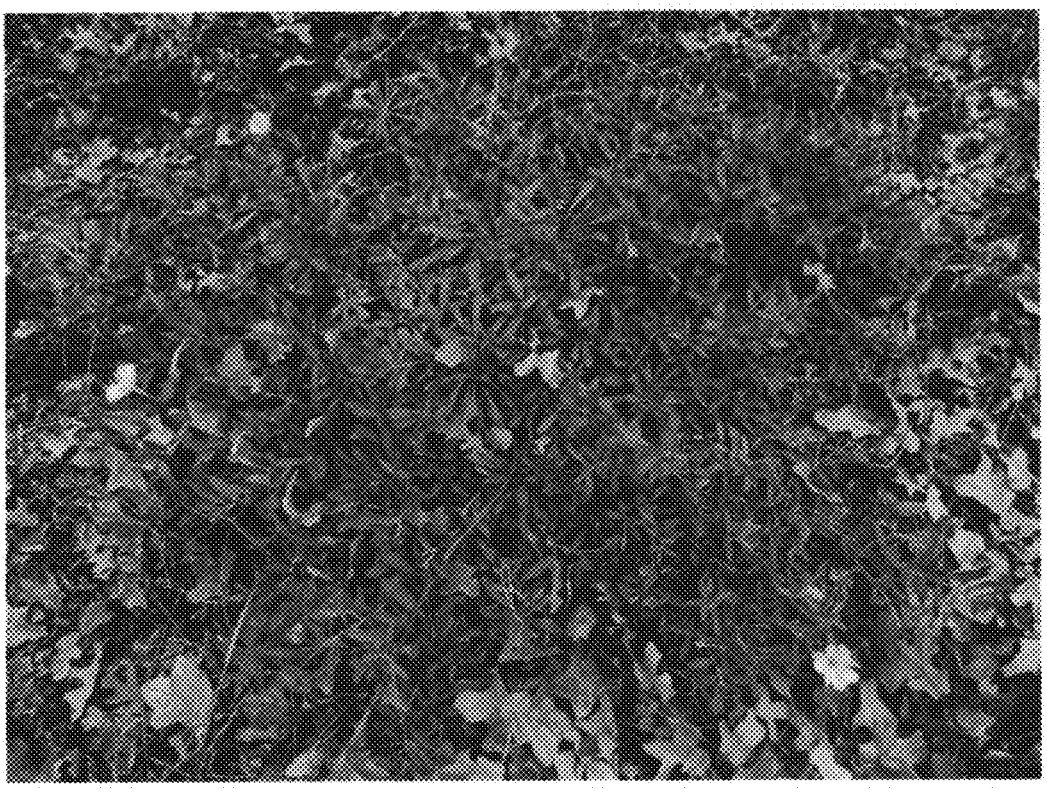
FIG. 6. Color photograph of mature plants in winter.
Figure 8:
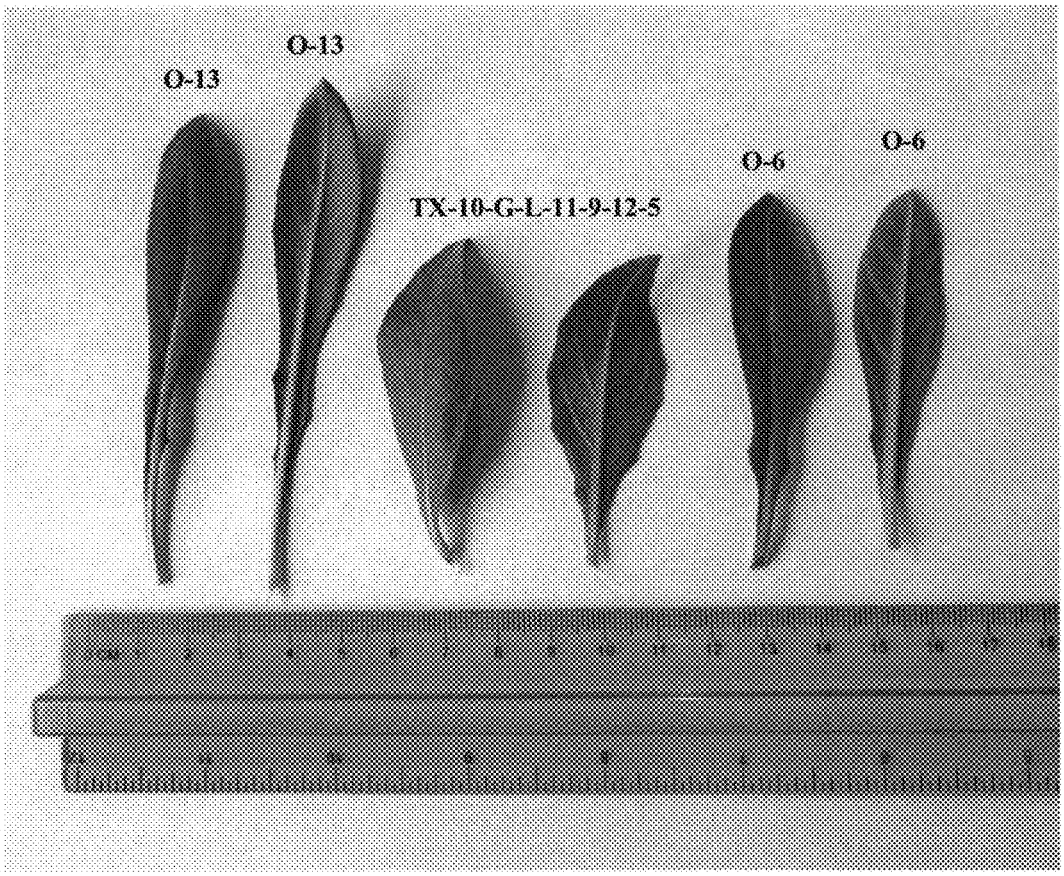
FIG. 8. Color photograph comparing leave shapes and surfaces of TX-10-G-L-11-9-12-5 in comparison to those of clones O-13 and O-6.
Figure 9:
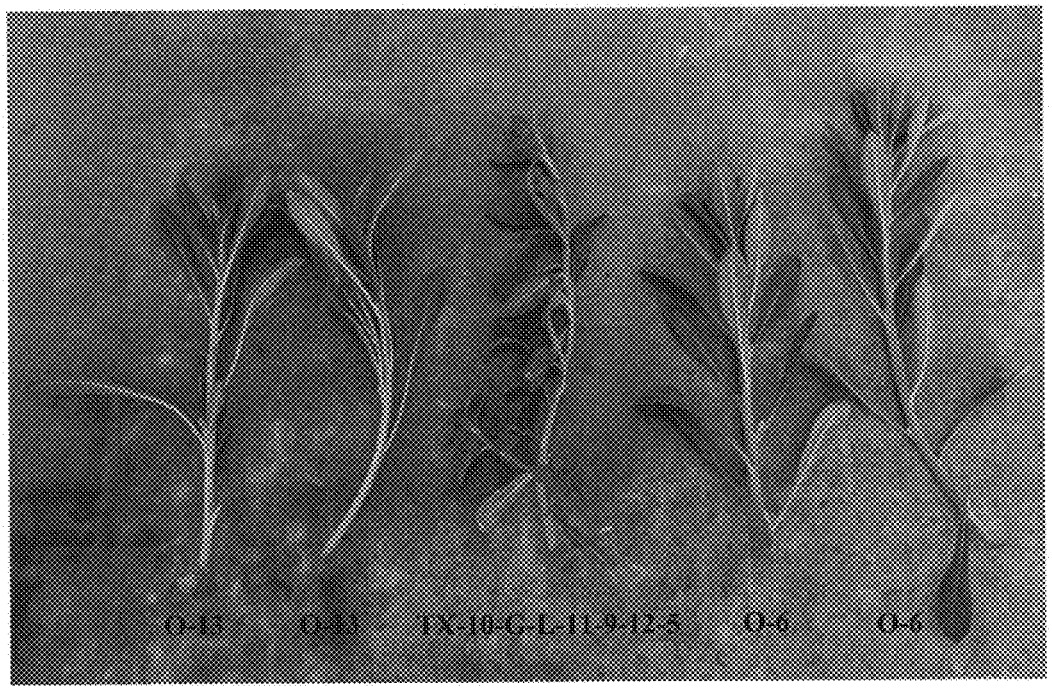
FIG. 9. Comparison of new growth of TX-10-G-L-11-9-12-5 in comparison to those of clones O-13 and O-6 illustrating broader leaves, shorter internodes, and more bud breaks of TX-10-G-L-11-9-12-5.

Foliage: Leaves of TX-10-G-L-11-9-12-5 are simple, evergreen to semi-evergreen, narrowly ovate to narrowly obovate; leaves of TX-10-G-L-11-9-12-5 are generally broader in relation to their length in comparison to those of other clones within the species which have more elongated leaves that are frequently obovate to nearly spatulate in shape and narrower in relation to their length as illustrated in the attached images; margins are entire to irregularly and very shallowly serrate, venation is pinnate, lightly impressed above and slightly to noticeably raised beneath; the background green of the leaves is covered to a greater or lesser degree of white to silver-white (R.H.S. N155A) hairs resulting in a slightly grey-green (R.H.S. N138B to N138C) overall leaf color above and slightly darker beneath (R.H.S. 147B). The density of foliage and horizontal crisscrossing of branching creates a solid canopy as a low groundcover which appears denser than the species type. FIG. 6 depicts TX-10-G-L-11-9-12-5, illustrating distinct low dense canopy (in winter). FIG. 8 is a comparison of TX-10-G-L-11-9-12-5, O-13, and O-6 leaf shapes and upper and lower surfaces, illustrating the broader width to length of leaves of TX-10-G-L-11-9-12-5 in comparison to O-13, and O-6. FIG. 9 is a comparison of TX-10-G-L-11-9-12-5, O-13, and O-6 new growth illustrating the denser foliage and broader width to length of leaves of TX-10-G-L-11-9-12-5 in comparison to that of O-13, and O-6.

*Arrangement.*—Alternate.

*Form.*—Simple, narrowly ovate, or more commonly narrowly obovate leaves.

*Size.*—Mature length on most young cutting propagated plants is 2 to 6 cm, but older more established plants can have narrow oblanceolate leaves to 13 cm long; leaf width its widest location typically ranges from 1 to 2 cm regardless of the length.

*Margins.*—Entire to irregularly and very, very shallowly serrate.

*Color.*—Top: light grey-green (R.H.S. N138B to N138C).

*Color.*—Bottom: medium grey-green (R.H.S. N147B).

*Veins.*—Venation is pinnate, lightly impressed above and slightly to noticeably raised beneath; veins are similar in color above and beneath the leaf with yellow-green (R.H.S. 154D) on main veins with grey-green (R.H.S. N138B) smaller veins.

*Petiole.*—Acute and 5 mm or less on new growth, maturing to 10 mm to 40 mm on older established plants, cuneate, light grey-green (R.H.S. N138B).

*Form.*—Low, typically less than 30 cm, with a spread of 60 to 90 cm during the first growing season; where grown as a perennial spread may reach 120 cm.

*Stipules.*—None.

Figure 3:
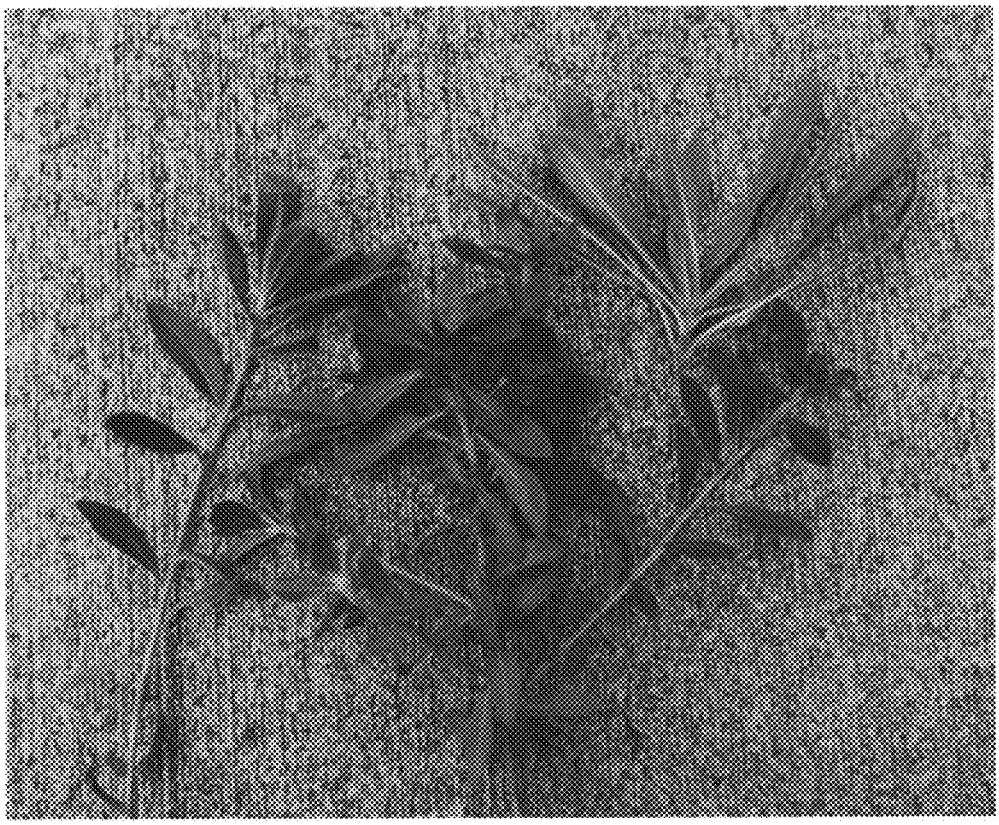
FIG. 3. Color photograph of leaves.
Figure 4:
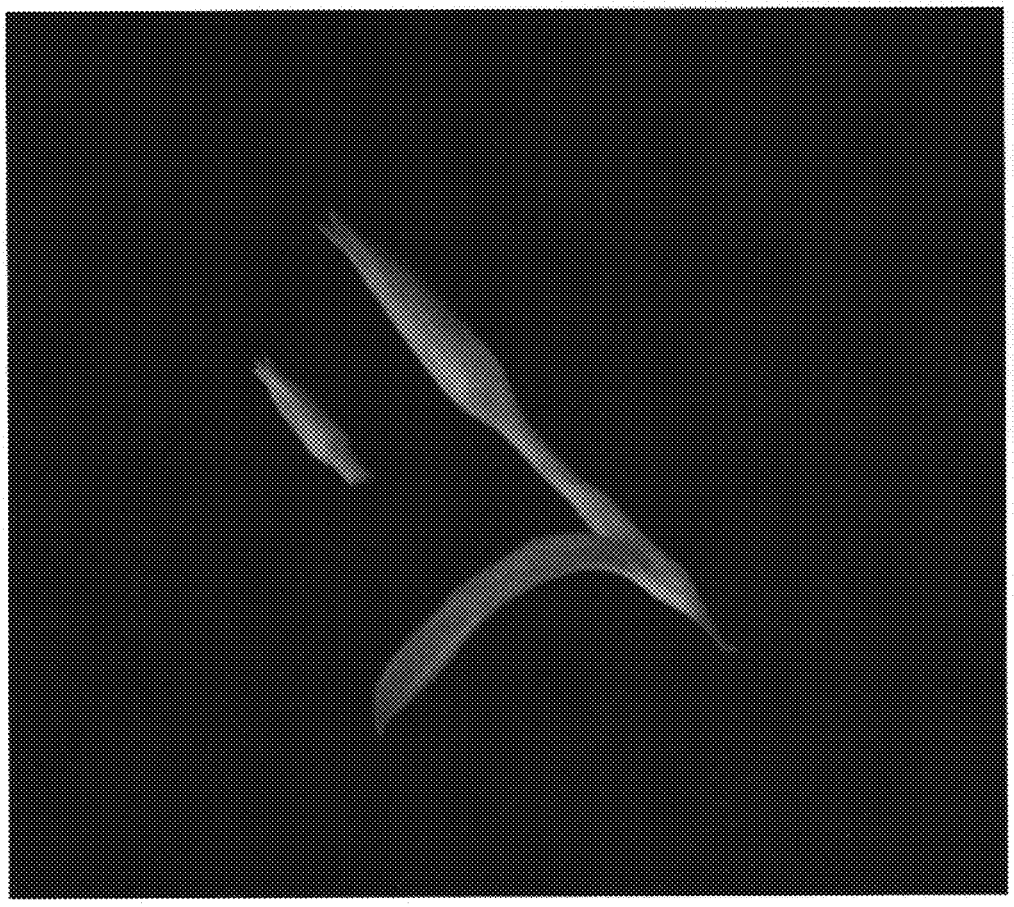
FIG. 4. Color photograph of developing flower buds.
Figure 7:
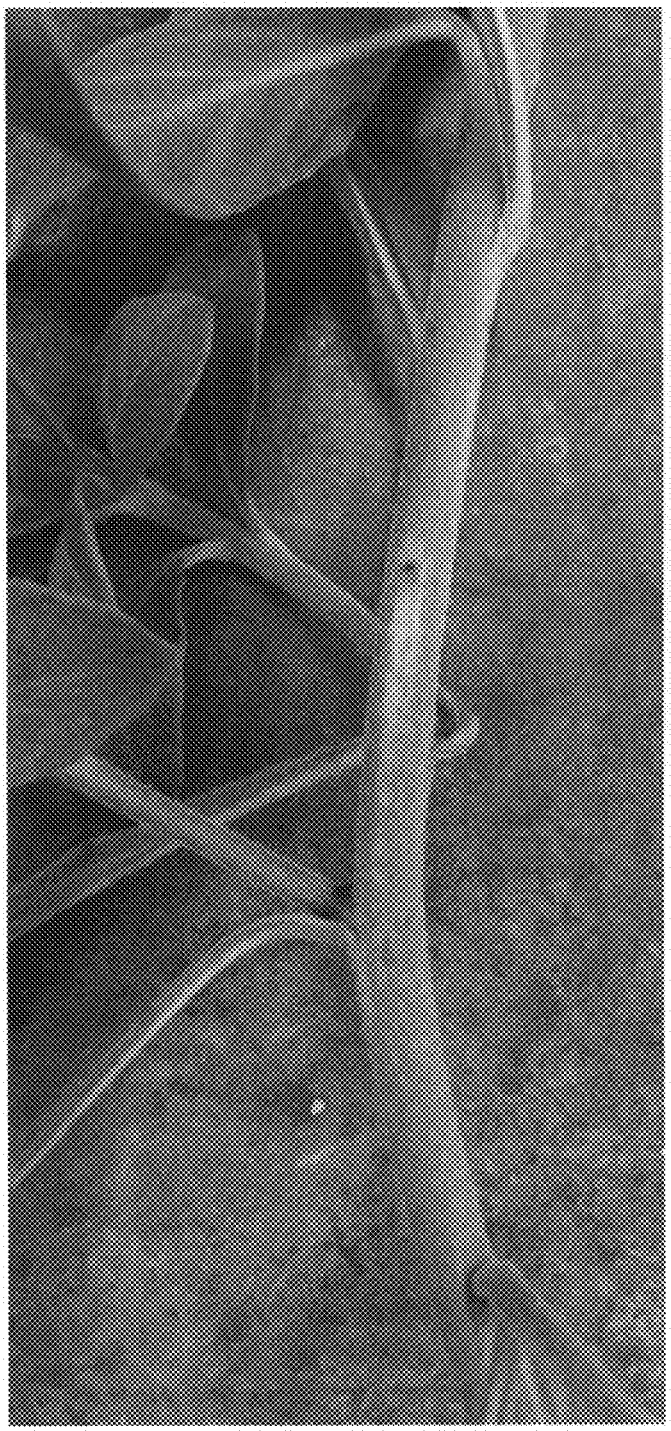
FIG. 7. Color photograph illustrating red stem color at nodes in cool season.

Stem: Mostly horizontal or arching in orientation, new growth of TX-10-G-L-11-9-12-5 is 5 to 7 mm in diameter, rounded in cross-section; the yellow-green (R.H.S. 145B) new stems may become flushed greyed-red (R.H.S. 181A) on upper surfaces as they age; this greyed-red color is often present at the base of buds on the nodes in comparison to the typical green of the species as illustrated in accompanying figures; vegetative buds tiny, hidden in the leaf axils until elongating; flower buds; mature stems eventually smooth with slight exfoliation bark with a greyed-yellow (R.H.S. 161C) to greyed-orange (R.H.S. 165B) color. FIG. 3 depicts TX-10-G-L-11-9-12-5, illustrating a red flush on mature stems in cool weather. FIG. 4 depicts flower bud development of TX-10-G-L-11-9-12-5. FIG. 7 illustrates the red portion of the stem at nodes, often present in cool weather.

Branching habit: Long arching to horizontal branches that crisscross to form a solid canopy.

Height: Typically less than 30 cm.

FLOWER

Blooming habit: Single large flowers held on long hypathia with the lower portion swelling to form the elongated cylindrical capsule-like fruits.

Corolla: Consisting of four petals attached to a common base with the sepals.

*Shape.*—Cup to saucer-shaped arrangement of petals which are not united.

Calyces: Initially four sepals are united to enclose the yellow-green (R.H.S. 144D) flower bud, later splitting along the margins to peel back as the flower opens.

*Number of sepals.*—Four.

*Color.*—(R.H.S. 144D).

Filaments: Eight in number, 14 to 16 mm long filament attaching midpoint to the anther; Color: (R.H.S. 2A).

Stamens: Eight in number, T-shaped, 14 to 16 mm long filament attaching midpoint to a 6 or 7 mm long thin cylindrical anther (R.H.S. 2A), total length is 15 to 18 mm attaching at the fused base of the petals and calyx.

Pistil: A 35 mm tall, strongly erect, very slender 1 to 2 mm diameter style is topped by a four lobbed stigma. The lobes are 1 mm in diameter, cylindrical, and held at a 45- to 90-degree angle to the style, both the style and stigma are of similar color as the petals (R.H.S. 2A).

Pollen: Viscin threads and clumping, similar in color to the staminal column (R.H.S. 2A).

Figure 2:
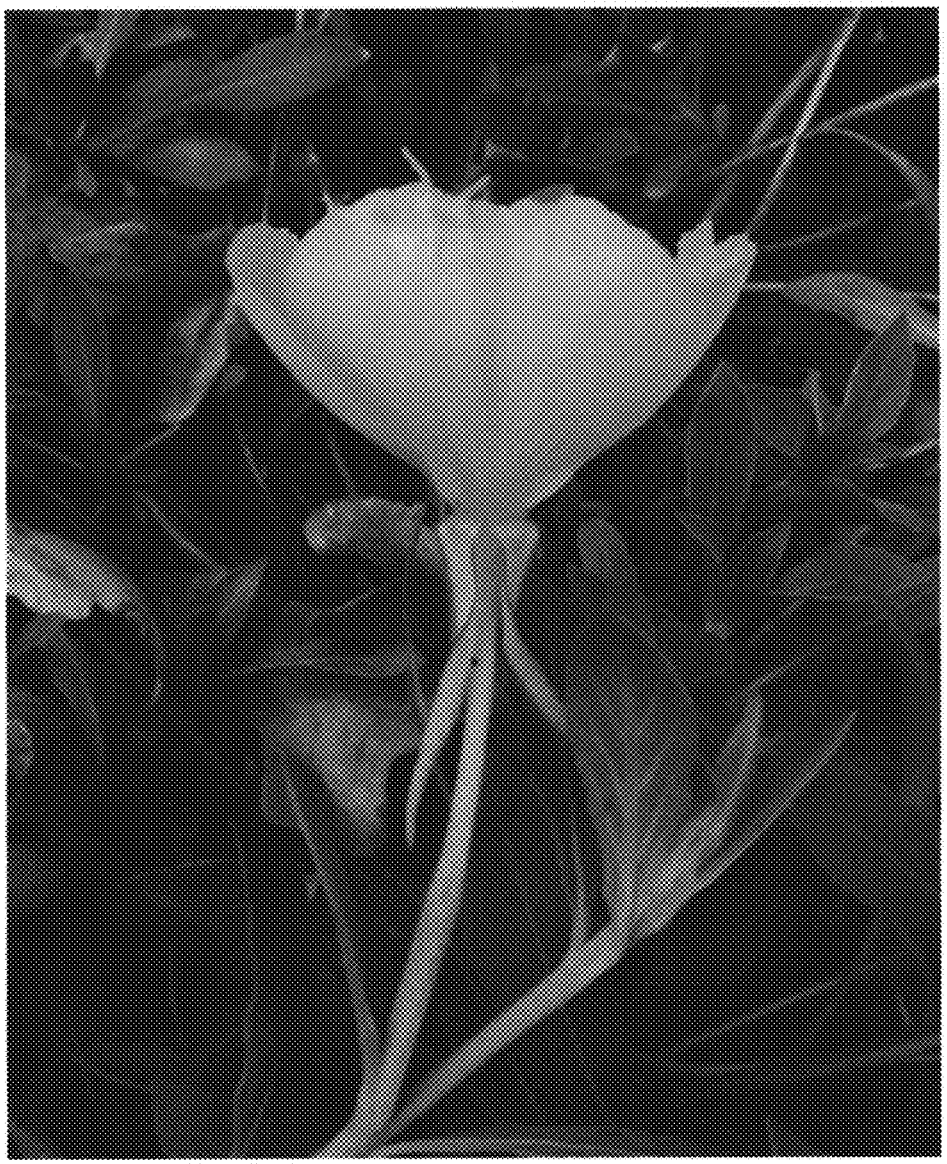
FIG. 2. Color photograph of side view of flower including sepals.

Petalage: Four petals attached at the base of the inflorescence to a fused small common base with the four subtending acuminate sepals which are initially in a conical, approximately 2.5 cm long, bud (R.H.S. 144D) are a fused calyx which split fully or incompletely along their margins and recurve; sepals are 2.5 to 3.0 cm long and taper from a 5 to 8 mm diameter base to a 1 to 2 mm tip and are a light green (R.H.S. 154A to 154B) with a 0.5 to 1.0 mm orange-red margin (R.H.S. N34A) except at the very tip which remains green (R.H.S. N134B). This orange-red margin on the sepals is unique to TX-10-G-L-11-9-12-5 and is not typically observed on other genotypes within *Oenothera drummondii*. FIG. 2 depicts a side view of a TX-10-G-L-11-9-12-5 flower, illustrating the unique features of overlapping petals forming a cup-shaped flower and the distinctive orange-red margins on the sepals and subtending grey-green foliage color. FIG. 10A depicts O-13, with arrows noting a separation of petals, lack of red suture lines on sepals. FIG. 10B depicts TX-10-G-L-11-9-12-5, with arrows noting mostly overlapping petals and red margins on sepals.

*Shape*.—Broadly ovate with a rounded to slightly emarginate tip and broadly acute base, margins are entire except at the tips where they may be minutely ruffled, the two vertical halves of the petal are slightly concave resulting in a shallow scooped inner side of the petals.

*Size*.—Petals are 3.0 to 3.5 cm in length by 3.5 to 4.0 cm in width at the broadest locations.

*Aspect*.—Overlapping to form a cup to open saucer-shaped bloom which differs from the separate petals of the species type which often overlap only slightly or have small gaps between the petal margins. FIG. 1 depicts a TX-10-G-L-11-9-12-5 flower from above, illustrating overlapping petals.

*Texture*.—Soft.

*Color*.—Waxy bright yellow (R.H.S. 2A) or sometimes after pollinated fading to a light tangerine orange color as they senesce.

Flower: The showy prominent petals, elongated pistil and stamens are all the same bright yellow (R.H.S. 2A) in color creating a highly conspicuous flower which typically opens in the late afternoon or evening and remains open into the next day or may remain open for several days; warm bright sunny days often shorten bloom period, whereas overcast cooler days result in the flower remaining open for longer periods; flowering of this cultivar appears to exhibit less of a photoperiodic response than the species type, flowering appears to be primarily limited by colder temperatures.

Hypathium: 5.0 to 5.5 cm long, cylindrical, 3 to 4 mm wide at the flower base, becoming swollen and ridged on the basal 2.0 to 2.5 cm as the seed capsule begins to develop; color grades from a yellow (R.H.S. 4C) close to the petals to a yellow-green (R.H.S. 149C) at the base.

GENERAL CHARACTERISTICS & CULTURE

Blooming period: Where temperatures permit, bloom occurs most of the year, bloom seems to be somewhat photoperiodic on the species type with greater bloom in long days/short nights, however TX-10-G-L-11-9-12-5 appears to be more free flowering, continuing to flower under shorter photoperiods than the species in general. FIG. 5 depicts TX-10-G-L-11-9-12-5, illustrating free flowering propensities (in spring).

Hardiness: Used as a summer annual in colder zones, but it has proven reliably winter hardy in USDA hardiness zones 8b, protected portions of 8a, through 13; established plants have survived 14° F. without significant injury.

Character in winter dormancy: Partially deciduous or semi-evergreen in colder margins of its hardiness zone, but where winter hardy it is typically evergreen.

Fragrance: None.

Figure 10:
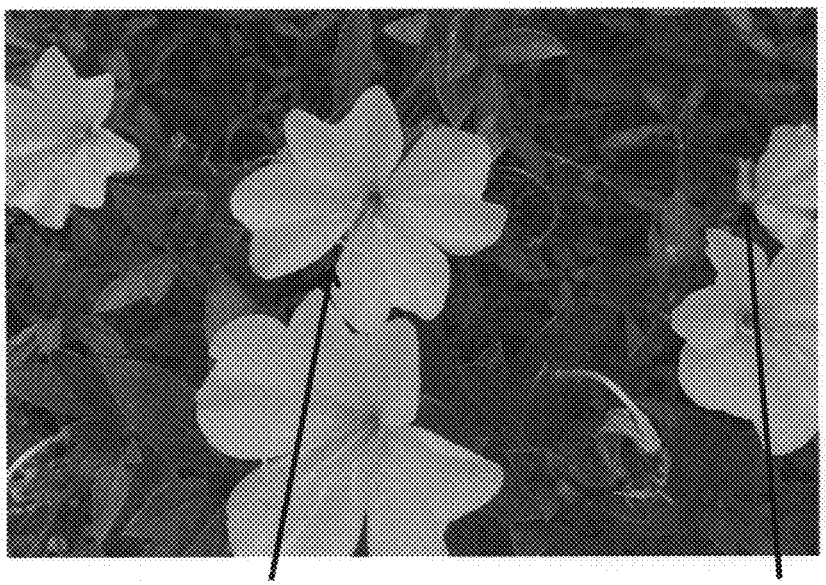
FIGS. 10A and 10B. Comparison of TX-10-G-L-11-9-12-5 petals, flowers, and sepals with those of O-13.
Figure 10:
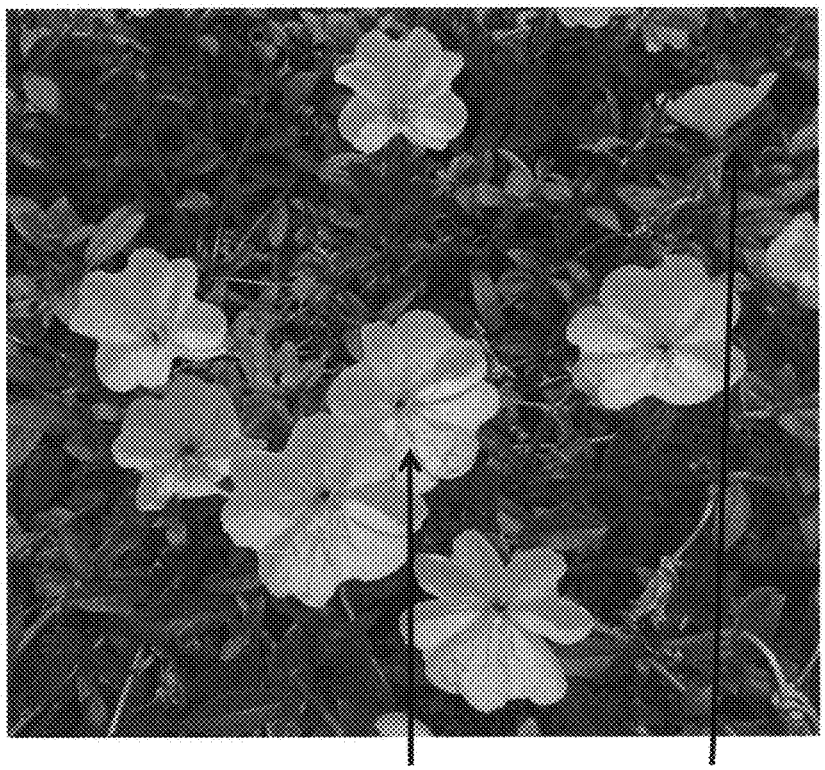
Figure 11:
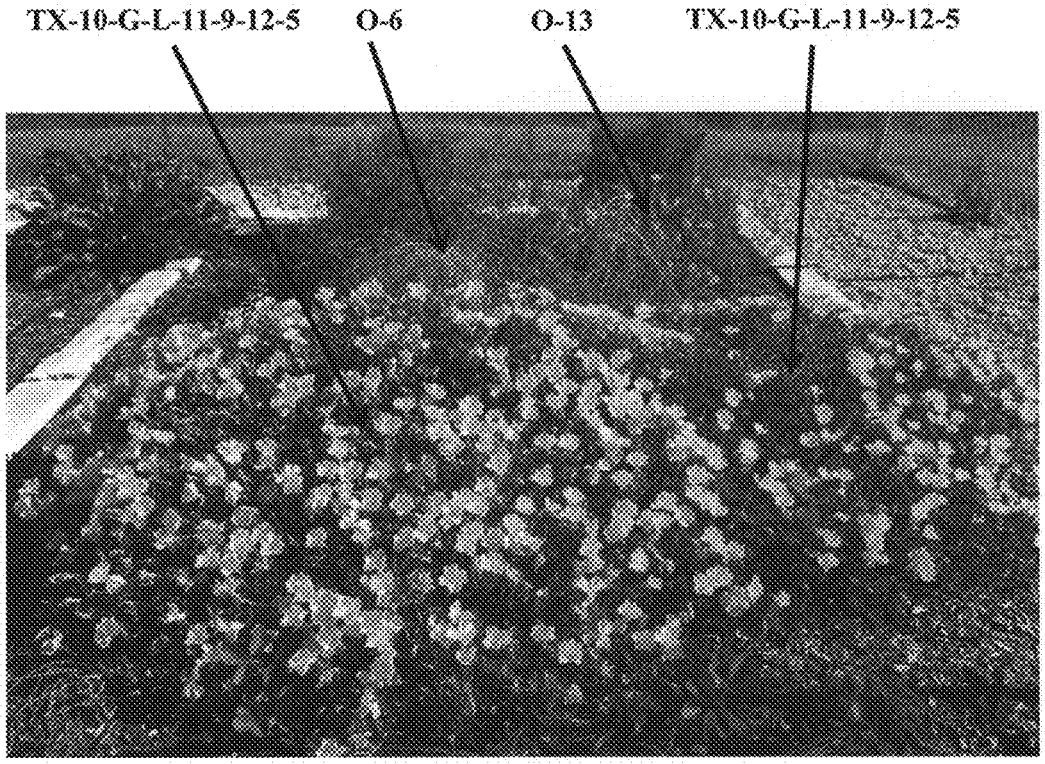
FIG. 11. Showing differential growth and flowering among TX-10-G-L-11-9-12-5, O-13, and O-6 in a *Phytophthora* infested trial bed.

Disease resistance: The species is prone to *Phytophthora* infestations in poorly drained soils or in heavy wet artificial substrates; this cultivar appears to be similar to, or somewhat less susceptible, than the species; TX-10-G-L-11-9-12-5 shows considerably less problems with root rots compared to the second-generation prior maternal parent plant and advanced clonal selections O-13 and O-6. FIG. 10 depicts TX-10-G-L-11-9-12-5 (front row, all vigorous and blooming), O-6 (middle row, all dead), and O-13 (last row, one plant still alive on far-right hand side with few blooms) growing in a *Phytophthora* infested trial bed.

Vigor: Vigor is strong with growth occurring rapidly under favorable conditions.

Breaking action: Stems elongate quickly with fairly long internodes, pinching during production increases earlier branching.

Rooting: Rooting occurs rapidly with or without auxin applications under light intermittent mist; well rooted cuttings can be produced from 7 to 10 cm terminal shoot cuttings within 10 to 14 days; best rooting is in a light, well aerated substrate such as 100% coarse perlite; leaving cuttings in mist benches for any significant period-of-time after rooting occurs often results in root rots and cutting mortality.

Growth regulator: None is required during rooting of shoot cuttings; best adventitious rooting of terminal shoot cuttings occurred without application of auxins or supplemental bottom heat (King, 2015). Paclobutrazol in the range of 30-35 mg active ingredient per 2.3-L container applied as a substrate drench should be effective in achieving approximately a one-third reduction in height and tightening up of the plant by reducing lateral internode extension and overall growth indices without overly stunting the plant during production (Carver, 2015).

Shipping tolerance: Rooted cuttings ship well; larger plants ship well if canopies are protected from breakage. Although the new variety TX-10-G-L-11-9-12-5 of *Oenothera drummondii* possesses the described characteristics when grown under the ecological conditions prevailing in central and south Texas, it will be understood that variations of the usual magnitude and characteristics incident to the changes in growing conditions, fertilization, pruning, and pest control are to be expected.

REFERENCES

Anon. 2001. R.H.S. Colour Chart. 4$^{th}$ Ed. The Royal Hort. Soc., London.

Carver, S. T. 2015. Evaluating the Ornamental Potentials of Four Native Texas Coastal Species. Ph.D. Dissertation, Texas A&M University, College Station, Tex. p. 155.

Carver, S. T., M. A. Arnold, D. H. Byrne, R. D. Lineberger, A. R. King, and A. R. Armitage. 2016. Variation in vegetative and floral characteristics of potential commercial significance in four native Texas coastal species. *Phytologia* 98(4): 250-276.

King, Andrew R. 2015. Ph.D. Investigating asexual propagation, container production, drought tolerance, and marketing strategies of five native Texas species. Ph.D. Dissertation, Texas A&M University, College Station, Tex. p. 300.

Richardson, A. 1990. Plants for Southmost Texas. Gorgas Science Foundation, Inc., Brownsville, Tex. p. 298.

We claim:

1. A new and distinct cultivar of *Oenothera drummondii* plant, substantially as illustrated and described herein.

* * * * *

A.

B.